US008034222B2

(12) United States Patent  (10) Patent No.: US 8,034,222 B2
Myung et al.  (45) Date of Patent: Oct. 11, 2011

(54) CONDUCTING POLYMER NANOWIRE SENSORS

(75) Inventors: Nosang V. Myung, Riverside, CA (US); Ashok Mulchandani, Riverside, CA (US); Wilfred Chen, Rowland Heights, CA (US)

(73) Assignee: The Regents of the University of California, Oakland, CA (US)

( * ) Notice: Subject to any disclaimer, the term of this patent is extended or adjusted under 35 U.S.C. 154(b) by 1409 days.

(21) Appl. No.: 11/259,557

(22) Filed: Oct. 25, 2005

(65) Prior Publication Data

US 2006/0207878 A1 Sep. 21, 2006

Related U.S. Application Data

(60) Provisional application No. 60/622,405, filed on Oct. 26, 2004.

(51) Int. Cl.
*G01N 27/327* (2006.01)
(52) U.S. Cl. ............... 204/403.01; 204/400; 422/82.02; 977/957
(58) Field of Classification Search .......... 204/400, 204/403.01, 403.09, 403.1, 403.14; 422/82.02; 977/957
See application file for complete search history.

(56) References Cited

U.S. PATENT DOCUMENTS 6,331,289 B1 * 12/2001 Klaveness et al. ........... 424/9.52
6,375,931 B2 * 4/2002 Østensen et al. ............. 424/9.52

OTHER PUBLICATIONS

Hernandez, Rose et al. "Template Fabrication of Protein-Functionalized Gold-Polypyrrole-Gold Segmented Nanowires." CHemistry of Materials, vol. 16, No. 18, (2004), pp. 3431-3438.*
Lillie et al, Sensors and Actuators B 78, 2001, pp. 249-256.*
Hernandez et al, Abstract of Papers, 225th ACS National Meeting, 2003.*
Huang et al, Chemistry A European Journal, 10, 2004, pp. 1314-1319.*
Bidan, Gerard; Electroconducting conjugated polymers: new sensitive matrices to build up chemical or electrochemical sensors. A review; 1992, *Sensors and Actuators* B, vol. 6, pp. 45-56.
Cui, Yi et al.; Nanowire Nanosensors for Highly Sensitive and Selective Detection of Biological and Chemical Species; 2001, *Science*, vol. 293, pp. 1289-1292.
Dai, Liming et al.; "Sensors and sensor arrays based on conjugated polymers and carbon nanotubes"; 2002, *Pur. Appl. Chem.*, vol. 74, No. 9, pp. 1753-1772.
Favier, Frederic et al.; "Hydrogen Sensors and Switches from Electrodeposited Palladium Mesowire Arrays"; 2001, *Science*, vol. 293, pp. 2227-2231.
Heeger, Alan J.; "Semiconducting and metallic polymers: the fourth generation of polymeric materials"; 2002, *Synthetic Metals*, vol. 125, pp. 23-42.
Kong, Jing et al.; "Nonotube Molecular Wires as Chemical Sensors"; 2000, *Science*, vol. 287, pp. 622-625.
Li, C.Z. et al.; "Molecular detection based on conductance quantization of nanowires" 2000, *Applied Physics Letters*, vol. 76, No. 10, pp. 1333-1335.
MacDiarmid, Alan G.; "Synthetic metals: a novel role for organic polymers"; 2002, *Synthetic Metals*, vol. 125, pp. 11-22.

(Continued)

*Primary Examiner* — Kaj K Olsen
(74) *Attorney, Agent, or Firm* — Kilpatrick Townsend & Stockton LLP

(57) ABSTRACT

Conducting polymer nanowires can be doped with analyte-binding species to create a nanowire that has a different conductivity depending on the presence or absence of the analyte.

8 Claims, 7 Drawing Sheets

OTHER PUBLICATIONS

Ramanathan, Kumaran et al.; "Application of poly(aniline) as a glucose biosensor" 1994, *Sensors and Actuators B*, vol. 21, pp. 165-169.

Ramanathan, K. et al.; "Individually Addressable Conducting Polymer Nanowires Array"; 2004, *Nano Letters*, vol. 4, No. 7, pp. 1237-1239.

Ramanathan, K. et al.; "Bioaffinity Sensing Using Biologically Functionalized Conducting-Polymer Nonowire"; 2005, *J. Am. Chem. Soc.*, vol. 127, pp. 496-497.

Schuhmann, Wolfgang; "Enzyme Biosensors Based on Conducting Polymers"; 1998, *Methods in Biology*, vol. 6, pp. 143-156.

Shirakawa, Hideki; "The discovery of polyacetylene film The dawning of an era of conducting polymers"; 2002, *Synthetic Metals*, vol. 125, pp. 3-10.

Yun, Minhee et al; "Electrochemically Grown Wires for Individually Addressable Sensor Arrays"; 2004, *Nanoletters*, vol. 4, No. 3, pp. 419-422.

Daniels-Hafer, Carrie et al.; "Tuning Charge Transport at the Interface between Indium Phosphide and a Polyprrole-Phosphomolybdate Hybrid through Manipulation of Electrochemical Potential"; 2002, *J. Phy. Chem. B*, vol. 106, pp. 1622-1636.

Esmaili, M. et al.; "An Enhancement to polypyrrole/chloride ion sensor performance"; 1996, *Smart Mater. Struct.*, vol. 5, pp. 437-440.

Lee, Hyo Joong et al.; "Electrochemistry of Conductive Polymers. 30. Nanoscale Measurements of Doping Distributions and Current-Voltage Characteristics of Electrochemically Deposited Polypyrrole Films"; 2004, *J. Phys. Chem. B*, vol. 108, pp. 1590-1595.

Lonergan, Mark C.; "A Tunable Diode Based on an Inorganic Semiconductor/Conjugated Polymer Interface"; 1997, *Science*, vol. 278, pp. 2103-2106.

Luckarift, Heather R. et al.; "Enzyme immobilization in a biomimetic silica support"; 2004, *Nature Biotechnology*, vol. 22, No. 2, pp. 211-213.

Park, J.G. et al.; "Current-voltage characteristics of polypyrrole nanotube in both vertical and lateral electrodes configuration"; 2003, *Thin Solid Films*, vol. 138-139, pp. 118-122.

Saha, S.K.; "Room-temperature single-electron tunneling in conducting polyprrole nanotube"; 2002, *Applied Physics Letters*, vol. 81, No. 19, pp. 3645-3647.

Saha, S.K.; "Current-voltage characteristics of conducting polypyrrole nanotubes using atomic force microscopy"; 2004, *Nanotechnology*, vol. 15, pp. 66-69.

\* cited by examiner

CONDUCTING POLYMER NANOWIRE SENSORS

CROSS-REFERENCES TO RELATED APPLICATIONS

The present application claims benefit of priority to U.S. Provisional Patent Application No. 60/622,405, filed Oct. 26, 2004, which is incorporated by reference for all purposes.

STATEMENT AS TO RIGHTS TO INVENTIONS MADE UNDER FEDERALLY SPONSORED RESEARCH OR DEVELOPMENT

The present invention was made with Government support under Grant No. DMEA90-02-2-0216, awarded by the U.S. Department of Defense. The Government has certain rights in this application.

TECHNICAL FIELD

Described herein are compositions and methods related generally to conducting polymer nanowires their synthesis and their uses as sensors.

BACKGROUND OF THE INVENTION

Recent advances in electronic detection based on nanowires (NWs) and nanotubes (NTs) has revolutionized our ability to provide label-free and real-time, yet sensitive and selective detection of a wide range of chemical and biological species using the NW or NT as the gate of a planar field effect transistor (FET). (Cui, Y. et al., *Science*, 293:1289-1292 (2001)) Unlike two-dimensional FETs, one-dimensional nanowires avoid the reduction in conductance changes caused by lateral current shunting to the point that even single-molecule detection is possible. The selectivity of the nanosensors can be further enhanced by modification with specific bioreceptors such as antibodies. For example, silicon nanowire (SiNWs) functionalized with biotin was used for highly sensitive, real-time and label-free detection of anti-biotin antibody. (Cui, Y. et al., *Science*, 293:1289-1292 (2001)). Similarly, human autoantigen (UTA) functionalized carbon nanotubes (CNT) were applied for label-free, sensitive and real-time detection of anti-UTA antibody. (Chen, R. J. et al., *PNAS*, 1000:4984-4989 (2003)) The suggested mechanism for the resulting high sensitivity is the extremely sensitive modulation of the electrical conductance/resistance of the NWs and NTs brought about by the changes in the electrostatic charges from surface adsorption of various molecules. The binding of analytes to the NWs or NTs leads to the depletion or accumulation of carriers in the "bulk" of the nanometer diameter structure and increases the sensitivity to potentially a single molecule.

While these reports demonstrated the power of nanoengineered materials as biosensors, the fabrication methods employed are seriously limited. The techniques of manipulating individual carbon nanotube onto pre-patterned electrodes by an atomic force microscope, (Roschier, L. et al., *P., Appl. Phys. Lett.*, 75:728-730 (1999)) random dispersion of suspended carbon nanotubes onto prepatterned electrodes (Tans, S. J. et al., *Nature*, 393:49-52 (1998); Bezryadin, A. et al., *Phys. Rev. Lett.*, 80:4036 (1998)) and lithographically patterning catalyst (as carbon nanotube nucleation sites) on electrodes (Franklin, N. R. et al., *Appl. Phys. Lett.*, 81:913-915 (2002); Guillorn, M. A. et al. *Appl. Phys. Lett.* 81:2860-2862 (2002)), while adequate for demonstrating the operational characteristics of individual devices, have low throughput and limited controllability and hence unattractive for scaling up to high-density sensor arrays. More importantly, surface modifications, typically required to incorporate bioreceptors, have to be performed post-synthesis and post-assembly. Attempts to improve fabrication controllability using either electric field alignment (Smith, P. A. et al., *Appl. Phys. Lett.*, 77:1399-1401 (2000); Duan, X. et al., *Nature*, 409:66-69 (2001)) or fluidic alignment followed by e-beam lithography have been reported. (Cui, Y. et al., *Science*, 293:1289-1292 (2001); Huang, Y. et al., *Science*, 294:1313-1317 (2001)) However, no report to-date has demonstrated the ability to assemble these nanomaterials into a functional sensor circuit and to individually address each nanostructured sensing elements with the desired bioreceptor, a requirement necessary for the successful fabrication of nanosensor arrays.

BRIEF SUMMARY OF THE INVENTION

Described herein are compositions, devices, and methods of making and using conducting polymer nanowire sensors for the detection of analytes. Generally, a conducting polymer nanowire sensor will show a change in a measurable electrical characteristic piezoelectric characteristic, or optical characteristic, including but not limited to electrical resistance, when contacted with a composition including the analyte to be detected. This allows detection of the analyte by monitoring an electrical characteristic of the conducting polymer nanowire sensor, and observing a change in the characteristic upon contact of the conducting polymer nanowire sensor with a composition containing the analyte.

The conducting polymer nanowire sensors are generally made of a conducting polymer material with an analyte-binding species incorporated into the conducting polymer material. Such conducting polymer material containing the analyte binding species may be referred to herein as "doped conducting polymer material," and nanowires made of doped conducting polymer material may be referred to as "doped conducting polymer nanowires," or "conducting polymer nanowire sensors."

In the Examples section below, are presented results for specific examples of the conducting polymer nanowire materials and nanowire sensors described herein and specific methods of making and using such materials and devices. First, however, are described conducting polymers that may be used in making the conducing polymer nanowires, analytes that may be detected and analyte-binding species that may be used to detect them, methods of making the doped conducting polymer nanowires, methods of detecting analytes using the doped conducting polymer nanowires, and devices incorporating the doped conducting polymer nanowires.

The present invention provides a doped conducting polymer material for detecting an analyte, the doped conducting polymer material comprising an analyte-binding species incorporated into a conducting polymer material.

In some embodiments, the analyte-binding species is capable of binding to an analyte. In some embodiments, an electrical characteristic of the doped conducting polymer material in contact with a composition comprising the analyte is different from the electrical characteristic of the doped conducting polymer material in contact with a composition substantially free of the analyte.

In some embodiments, the analyte-binding species and analyte are selected from the group consisting of natural and synthetic antibodies and antibody fragments and their corresponding antigens; natural and synthetic proteins and protein fragments and their corresponding ligands; receptors and their ligands; natural and synthetic polynucleotide and oligonucleotide sequences and their complementary sequences; single and multiple strand, natural and synthetic nucleic acids and species binding to such single and multiple strand nucleic acids; and DNA aptamers and their ligands.

In some embodiments, the conducting polymer material is polyacetylene, polyaniline, polythiophene, polypyrrole, polyarylene, polyphenylene, poly(bisthiophenephenylene), poly-methylpyrrole, conjugated ladder polymer, poly(arylene vinylene), poly(arylene ethynylene), various organic derivatives of these polymers, organometallic derivatives of these polymers, or inorganic derivatives of these polymers.

In some embodiments, the polymer material is polypyrrole.

In some embodiments, the analyte-binding species is avidin or a derivative of avidin.

In some embodiments, the analyte is biotin or a derivative of biotin.

In some embodiments, the composition to be contacted with the doped conducting polymer material is a solid composition, a gaseous composition, a powdered solid composition, or an aerosolized composition.

In some embodiments, the electrical characteristic is the resistance.

The present invention also provides A device for detecting an analyte, the device comprising first and second electrodes; one or more doped conducting polymer nanowires connecting the first and second electrodes, and a circuit for monitoring an electrical characteristic between the first and second electrodes.

In some embodiments, one or more doped conducting polymer nanowires are made of a doped conducting polymer material comprising an analyte-binding species incorporated into a conducting polymer material.

In some embodiments, the analyte-binding species is capable of binding to an analyte; and the electrical characteristic of the doped conducting polymer material in contact with a composition comprising the analyte is different from the electrical characteristic of the doped conducting polymer material not in contact with a composition substantially free of the analyte.

In some embodiments, the analyte-binding species and analyte are selected from the group consisting of natural and synthetic antibodies and antibody fragments and their corresponding antigens; natural and synthetic proteins and protein fragments and their corresponding ligands; receptors and their ligands; natural and synthetic polynucleotide and oligonucleotide sequences and their complementary sequences; single and multiple strand, natural and synthetic nucleic acids and species binding to such single and multiple strand nucleic acids; and DNA aptamers and their ligands.

In some embodiments, the conducting polymer material is selected a polyacetylene, polyaniline, polythiophene, polypyrrole, polyarylene, polyphenylene, poly(bisthiophenephenylene), poly-methylpyrrole, conjugated ladder polymer, poly(arylene vinylene), poly(arylene ethynylene), various organic derivatives of these polymers, organometallic derivatives of these polymers, or inorganic derivatives of these polymers.

In some embodiments, the polymer material is polypyrrole.

In some embodiments, the analyte-binding species is avidin or a derivative of avidin.

In some embodiments, the analyte is biotin or a derivative of biotin.

In some embodiments, the composition to be contacted with the doped conducting polymer material is a solid composition, a gaseous composition, a powdered solid composition, or an aerosolized composition.

In some embodiments, the electrical characteristic is the resistance.

The present invention provides a method for making a conducting polymer nanowire, the method comprising placing in a space between a first and second electrode a composition comprising a conducting polymer monomer polymerizable by electrochemical polymerization; causing a current to flow between the first and second electrodes, thereby causing the composition to polymerize and form a conducting polymer nanowire; monitoring the potential of one or more of the electrodes; and removing the current between the first and second electrodes when the monitored potential drops to approximately zero, indicating formation of a conducting polymer nanowire connecting the first and second electrodes.

In some embodiments, the conducting polymer monomer is a monomer that upon electrochemical polymerization gives polyacetylene, polyaniline, polythiophene polypyrrole, polyarylene, polyphenylene, poly(bisthiophenephenylene), polymethylpyrrole, conjugated ladder polymer, poly(arylene vinylene), poly(arylene ethynylene), various organic derivatives of these polymers, organometallic derivatives of these polymers, or inorganic derivatives of these polymers.

In some embodiments, the conducting polymer monomer is a monomer that upon electrochemical polymerization gives polypyrrole.

The present invention also provides a method for making a doped conducting polymer nanowire, the method comprising placing in a space between a first and second electrode a composition comprising a conducting polymer monomer polymerizable by electrochemical polymerization and a dopant species; causing a current to flow between the first and second electrodes, thereby causing the composition to polymerize and form a doped conducting polymer nanowire; monitoring the potential of one or more of the electrodes; and removing the current between the first and second electrodes when the monitored potential drops to approximately zero, indicating formation of a doped conducting polymer nanowire connecting the first and second electrodes.

In some embodiments, the dopant species is an analyte-binding species capable of binding to an analyte; and wherein an electrical characteristic of the doped conducting polymer nanowire in contact with a composition comprising the analyte is different from the electrical characteristic of the doped conducting polymer nanowire in contact with a composition substantially free of the analyte.

In some embodiments, the analyte-binding species and analyte are selected from the group consisting of natural and synthetic antibodies and antibody fragments and their corresponding antigens; natural and synthetic proteins and protein fragments and their corresponding ligands; receptors and their ligands; natural and synthetic polynucleotide and oligonucleotide sequences and their complementary sequences; single and multiple strand, natural and synthetic nucleic acids and species binding to such single and multiple strand nucleic acids; and DNA aptamers and their ligands.

In some embodiments, the conducting polymer monomer is a monomer that upon electrochemical polymerization gives polyacetylene, polyaniline, polythiophene, polypyrrole, polyarylene, polyphenylene, poly(bisthiophenephenylene), polymethylpyrrole, conjugated ladder polymer, poly(arylene vinylene), poly(arylene ethynylene), various organic derivatives of these polymers, organometallic derivatives of these polymers, or inorganic derivatives of these polymers.

In some embodiments, the conducting polymer monomer is a monomer that upon electrochemical polymerization gives polypyrrole.

In some embodiments, the analyte-binding species is avidin or a derivative of avidin.

In some embodiments, the analyte is biotin or a derivative of biotin.

In some embodiments, the composition comprising to be contacted with the doped conducting polymer material is a solid composition, a gaseous composition, a powdered solid composition, or an aerosolized composition.

In some embodiments, the electrical characteristic is the resistance.

DETAILED DESCRIPTION OF THE INVENTION

Conducting Polymers

Figure 1:
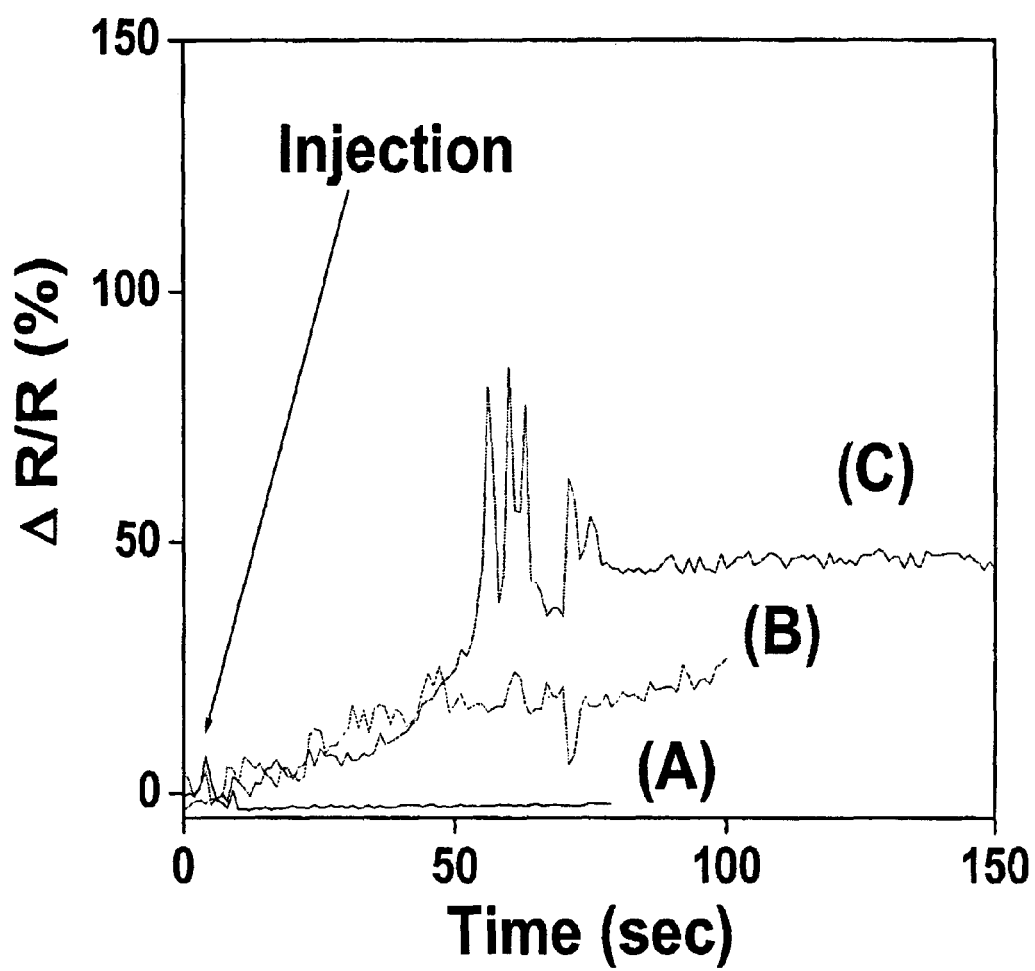
FIG. 1 shows the electrical responses of Avidin embedded polypyrrole (200 nm) to additions of 1 µL of A) 1 nM biotin-DNA (single stranded) and B) 100 nM biotin-DNA.

Generally the doped conducting polymer nanowires may be made using any conducting polymer into which analyte-detecting species may be incorporated, which may be formed into a doped conducting polymer nanowire, and for which an electrical characteristic changes upon contact of the doped nanowire with the analyte. Specific examples of conducting polymer material that may be used include but are not limited to the methods described in the Examples.

Conducting polymer materials that may be used include but are not limited to polyacetylene, polyaniline, polythiophene, polypyrrole, polyarylene, polyphenylene, poly (bisthiophenephenylene), poly-methylpyrrole, conjugated ladder polymer, poly(arylene vinylene), poly(arylene ethynylene), various organic derivatives of these polymers, organometallic derivatives of these polymers, or inorganic derivatives of these polymers. Other conducting polymers that may be used are described in Handbook of Conducting Polymers, by Tede A. Skotheim, Ronald L. Elsenbaumer, John R. Reynolds, Marcel Dekker; 2nd Rev&Ex edition (Nov. 1, 1997), the contents of which are incorporated herein in their entirety. In one doped conducting polymer, the polymer is polypyrrole. In one doped conducting polymer, the polymer is polyaniline. In one doped conducting polymer, the polymer is poly-methylpyrrole.

Analytes and Analyte-Binding Species

Generally, the doped conducting polymer materials described herein may be used for detecting any analyte that is capable of affecting an electrical characteristic of the doped conducting polymer materials when the analyte is contacted with such material. Specific examples of analytes include but are not limited to those described in the Examples.

The analyte to be detected may generally be in any type of physical form that is capable of contacting with the doped conducting polymer materials in such a way as to allow the analyte to affect an electrical characteristic of the material. Specific examples include but are not limited to the analyte physical forms described in the Examples. The analyte may be present in a variety of physical forms including but not limited to a solution of the analyte, a gaseous form of the analyte, an aerosolized form of the analyte, a solid form of the analyte, and a solid powdered form of the analyte. In each of these physical forms, the analyte composition may be made of pure analyte or may contain the analyte together with additional components.

Regarding the analyte-binding species, generally any species may be used that is capable of being incorporated into the conducting polymer material, and that changes an electrical characteristic of the doped conducting polymer material when such material is contacted with a composition containing the analyte. Specific examples of analyte binding species include but are not limited to those described in the Examples.

In one doped conducting polymer material, the analyte binding species is a species that is capable of binding to the analyte. Such binding can be by a variety of mechanisms including but not limited to covalent bonding, ionic bonding, hydrogen bonding, van der Waals bonding, bonding by dispersion forces, hydrophilic and hydrophobic interactions, and combination of these bonding mechanisms.

Analyte and analyte-binding species that may be used include but are not limited to natural and synthetic antibodies and antibody fragments and their corresponding antigens; natural and synthetic proteins and protein fragments and their corresponding ligands, including but not limited to small molecule, cofactor, and natural and synthetic protein, peptide, and peptide fragment ligands; receptors and their ligands, including but not limited to small molecule, cofactor, and natural and synthetic protein, peptide, and peptide fragment ligands; natural and synthetic polynucleotide and oligonucleotide sequences and their complementary sequences; single and multiple strand, natural and synthetic nucleic acids and species binding to such single and multiple strand nucleic acids; and DNA aptamers and their ligands.

In one doped conducting polymer material, the analyte is a charged biological molecule and the analyte-binding species is any species capable of binding to the charged biological molecule.

For each of the analyte and analyte-binding species listed above, it is also possible to reverse the roles of the two species; that is, the species listed as the analyte can be used as an analyte-binding species and the species listed as an analyte-binding species can be used as an analyte. For example, and in non way limiting, if it is possible to detect an analyte that is a small molecule ligand of a protein using a conducting polymer nanowire doped with the protein to which the small molecule is a ligand, it is expected to be possible to detect an analyte that is a protein using a conducting polymer nanowire doped with the small molecule ligand of the protein. As a specific example, and in no way limiting, in the examples below biotin is the analyte and avidin is the analyte-binding species; however, it is expected to be possible to use avidin as the analyte and biotin as the analyte-binding species.

In one doped conducting polymer material, the analyte-binging species is a natural or synthetic protein or protein fragment, and the analyte is a ligand to the protein or protein fragment. In one doped conducting polymer material, the analyte-binging species is a natural or synthetic protein or protein fragment, and the analyte is a protein, peptide, or peptide fragment ligand to the protein or protein fragment. In one doped conducting polymer material, the analyte-binging species is a natural protein or fragment of a natural protein, and the analyte is a protein, peptide, or peptide fragment ligand to the protein or protein fragment.

In one doped conducting polymer material, the analyte is a natural or synthetic protein or protein fragment, and the analyte-binging species is a ligand to the protein or protein fragment. In one doped conducting polymer material, the analyte is a natural or synthetic protein or protein fragment, and the analyte-binging species is a protein, peptide, or peptide fragment ligand to the protein or protein fragment. In one doped conducting polymer material, the analyte is a natural protein or fragment of a natural protein, and the analyte-binging species is a protein, peptide, or peptide fragment ligand to the protein or protein fragment.

Methods of Making Doped Conducting Polymer Nanowires

Generally the doped conducting polymer nanowires may be made by any method capable of incorporating the analyte-binding species into the conducting polymer material and forming such into a conducting polymer nanowire. Specific examples include but are not limited to the methods described in the Examples.

In one method of making doped conducting polymer nanowires, the method comprising placing in a space between a first and second electrode a composition comprising a conducting polymer monomer polymerizable by electrochemical polymerization and a dopant species; causing a current to flow between the first and second electrodes, thereby causing the composition to polymerize and forming a doped conducting polymer nanowire; monitoring the potential of one or more of the electrodes; and removing the current between the first and second electrodes when the monitored potential drops to approximately zero, indicating formation of a doped conducting polymer nanowire connecting the first and second electrodes. When the doped conducting polymer nanowire will be used for detecting an analyte, the dopant species is an analyte-binding species.

In another method of making doped conducting polymer nanowires, additional components may be added to the conducting polymer material along with the analyte-binding species.

Geometric and Other Characteristics of Doped Conducting Polymer Nanowires

Generally, the doped conducting polymer nanowires maybe of any size and geometry that may be produced using the methods described herein, including but not limited to the methods described in the Examples. Sizes and geometries include but are not limited to those described in the Examples.

In one doped conducting polymer nanowire, the nanowire is approximately tube shaped with a diameter of less than about 200 nm, and a length of about 100 µm or less. In one doped conducting polymer nanowire, the nanowire has an approximately rectangular or eliptical cross section and has a depth of about 200 nm or less, a width of about 500 nm or less, and a length of about 100 µm or less. In one doped conducting polymer nanowire, the nanowire has an approximately rectangular or eliptical cross section and has a depth of about 200 nm or less, a width of about 200 nm or less. In one doped conducting polymer nanowire, the nanowire has an approximately rectangular or eliptical cross section and has a depth of about 100 nm or less, a width of about 100 nm or less. In one doped conducting polymer nanowire, the nanowire has an approximately spherical cross section and has a diameter of about 200 nm or less. In one doped conducting polymer nanowire, the nanowire has an approximately spherical cross section and has a diameter of about 100 nm or less. In one doped conducting polymer nanowire, the nanowire has an approximately spherical cross section and has a diameter of about 50 nm or less. In one doped conducting polymer nanowire, the nanowire has an approximately spherical cross section and has a diameter of about 20 nm or less. In one doped conducting polymer nanowire, the nanowire has an approximately rectangular or eliptical cross section and has a depth of about 50 nm or less, a width of about 50 nm or less. In one doped conducting polymer nanowire, the nanowire has an approximately rectangular or eliptical cross section and has a depth of about 20 nm or less, a width of about 20 nm or less. In one doped conducting polymer nanowire, the nanowire has any of the cross-sectional geometries and sizes described above and has a length of about 50 µm or less. In one doped conducting polymer nanowire, the nanowire has any of the cross-sectional geometries and sizes described above and has a length of about 20 µm or less. In one doped conducting polymer nanowire, the nanowire has any of the cross-sectional geometries and sizes described above and has a length of about 10 µm or less. In one doped conducting polymer nanowire, the nanowire has any of the cross-sectional geometries and sizes described above and has a length of about 5 µm or less. In one doped conducting polymer nanowire, the nanowire has any of the cross-sectional geometries and sizes described above and has a length of about 3 µm or less.

Methods of Detecting Analytes using Doped Conducting Polymer Nanowires

Generally, the doped conducting polymer nanowires are used for detecting analytes by monitoring a characteristic including but not limited to an electrical characteristic a piezoelectrical characteristic, or an optical characteristic of one or more of the doped conducting polymer nanowires and identifying the presence of the analyte being detected when a change in the electrical characteristic is observed. Specific methods that may be used include but are not limited to those described in the Examples.

Electrical characteristics that may be monitored to detect analytes are generally any characteristic that may be measured and that shows a measurable change when the conducting polymer nanowire sensor is contacted with a composition containing analytes. Specific electrical characteristics that may be used include but are not limited to the electrical characteristics described in the Examples. In one method of detecting analytes using doped conducting polymer nanowires, the electrical resistance of one or more doped conducting polymer nanowires is measured. In another method of detecting analytes using doped conducting polymer nanowires, the electrical current of one or more doped conducting polymer nanowires is measured. In another method of detecting analytes using doped conducting polymer nanowires, the voltage drop across one or more doped conducting polymer nanowires is measured.

The quantitative effect of the analyte on the measured electrical characteristic may depend on the amount of analyte with which the one or more doped conducting polymer nanowires are contacted. In such a case, the doped conducting polymer nanowires may be used to measure the quantity of analyte present.

Devices Incorporating Doped Conducting Polymer Nanowires

Generally, the doped conducting polymer nanowires may be incorporated into any device in which one or more of the doped conducting polymer nanowires may be contacted with the material to be analyzed and in which an electrical characteristic of one or more of the doped conducting polymer nanowires may be monitored. Specific devices that may be used include but are not limited to those described in the Examples.

In one device described herein, the device includes a first electrode, a second electrode, one or more doped conducting polymer nanowires attached to the first and electrodes, and a circuit for monitoring an electrical characteristic between the first and second electrode. Generally, such a device may be made by any method capable of producing one or more doped conducting polymer nanowires attached to the first and electrodes. Specific methods of making such devices that may be used include but are not limited to those described in the Examples.

In one method of making such devices, the method includes the steps of (Cui, Y. et al., *Science*, 293:1289-1292 (2001)) placing in a space between a first and second electrode a composition comprising a conducting polymer monomer polymerizable by electrochemical polymerization and a dopant species; (Chen, R. J. et al., *PNAS*, 1000:4984-4989 (2003)) causing a current to flow between the first and second electrodes, thereby causing the composition to polymerize and form a conducting polymer nanowire; (Roschier, L. et al., *P., Appl. Phys. Lett.*, 75:728-730 (1999)) monitoring the potential of one or more of the electrodes; and (Tans, S. J. et al., *Nature*, 393:49-52 (1998)) removing the current between the first and second electrodes when the monitored potential drops to approximately zero, indicating formation of a conducting polymer nanowire connecting the first and second electrodes. This method may be used for producing a device containing first and second electrodes with a doped conducting polymer nanowire connecting the two electrodes. When the dopant species is an analyte-binding species, the device may be used for detecting an the presence of the analyte in a composition.

The above method of making a nanowire attached to first and second electrodes may also be carried out in to absence of a dopant species to produce an undoped conducting polymer nanowire connecting the two electrodes.

One device described herein includes doped conducting polymer nanowires containing different analyte-binding species. By monitoring electrical characteristics of the differently doped nanowires, such a device can be used for detecting a number of different analytes. By way of example only and in no way limiting, if doped conducting nanowire 1 contains species capable of bonding to analyte 1 and doped conducting nanowire 2 contains species capable of bonding to analyte 2, the device may be used for detecting the presence of analyte 1 and analyte 2, The examples and embodiments described in this patent are for illustrative purposes only. Various modifications or changes will be suggested to persons skilled in the art and are to be included within the disclosure in this application and scope of the claims. All publications, patents and patent applications cited in this patent are hereby incorporated by reference in their entirety for all purposes to the same extent as if each individual publication, patent or patent application were specifically and individually indicated to be so incorporated by reference.

EXAMPLE 1

Bioaffinity Sensing Using Biologically-Functionalized Conducting Polymer Nanowire The following is an example that has been carried out of the synthesis and use of one conducting polymer nanowire sensor as described in this patent.

A simple one-step method for fabricating single biologically-functionalized conducting polymer (polypyrrole) nanowire on prepatterned electrodes and its application to biosensing was demonstrated. The biologically functionalized polypyrrole was formed by the electropolymerization of an aqueous solution of pyrrole monomer and the model biomolecule, avidin or streptavidin conjugated ZnSe/CdSe quantum dots, within 100 or 200 nm wide by 3 µm long channels between gold electrodes on prefabricated silicon substrate. When challenged with biotin-DNA, the avidin- and streptavidin-polypyrrole nanowires generated a rapid change in resistance to as low as 1 nM demonstrating the utility of the biomolecule-functionalized nanowire as biosensor. The method offers advantages of direct incorporation of functional biological molecules into the conducting-polymer nanowire during its synthesis, site-specific positioning, built-in electrical contacts and scalability to high density nanoarrays over the reported silicon nanowires and carbon nanotubes biosensors.

Conducting polymers such as polypyrrole (Ppy) because of their electronic conductivity, environmental stability, easy and controlled processing by electrochemical polymerization and biocompatibility have emerged as promising materials in the development of planar electrochemical biosensors. Biomolecules can be incorporated into the conducting polymer in a single-step during polymer synthesis rather than multiple steps needed in surface-modified silicon nanowires and carbon nanotubes. Recently, Hernandez et al. reported a template method for synthesis of biologically-functionalized Ppy nanowires. (Hernandez, R. M. et al., *Chem. Mater.*, 16:3431-3438 (2004)) Although elegant, application of template fabricated biologically functionalized nanowire is limited by some of the same problems as SiNWs and CNT. Because the nanowires synthesized in the template have to be separated and collected by dissolving the template in a solution, the nanowires are either floating or remain attached to the substrate forming a vertical array. For use in biosensor these nanowires will need time-consuming and arduous method of contacting onto patterned electrodes. Additionally, the harsh conditions, 25% nitric acid followed by 3 M sodium hydroxide, required to dissolve the alumina template might not be suitable for many biological molecules of interest. We report herein for the first time a simple, biomolecule-friendly, single-step protocol for the fabrication of polypyrrole nanowire biosensor of controlled dimension and composition, large aspect ratio and most of all site-specific positioning and its application to label-free bioaffinity sensing.

We recently demonstrated the feasibility of fabricating single and multiple individually addressable polypyrrole and polyaniline nanowires of controlled dimension (100 nm wide and up to 13 µm long) and location by electrodeposition within a channel between two electrodes on the surface of a silicon wafer and their application as pH sensors. (Ramanathan, K. et al., *Nano Lett.*, 4:1237-1239 (2004)) A similar electrode structure with 100 or 200 nm wide by 3 µm long channel was employed for the entrapment of the model protein, avidin, during electrochemical polymerization of polypyrrole in a single step. In a typical experiment 2 µl of a deoxygenated pyrrole (25 mM in 10 mM NaCl in deionized water) solution without or with 2 nM avidin or streptavidin-coated ZnSe/CdSe quantum dot (Aqd) were placed in the electrolyte channel between the two electrodes. The electro-oxidative polymerization of pyrrole was performed in the galvanostatic mode by applying a 100 nA current while the working electrode potential was monitored continuously with respect to a pseudo reference electrode. The initial investigations on biomolecule-functionalization of Ppy nanowires by entrapment in a single-step during electropolymerization were performed using Aqd. This was done to facilitate microscopic characterization and establishing the location of the biomolecule in the nanowire.

A typical chronopotentiogram during growth of the Aqd-functionalized Ppy nanowires showed the potential jumped from open circuit to a value between 2.8 and 2.9 V followed by a gradual decrease for ~4 sec as the wire grew and a sharp drop to ~0 V when the first contact was made with the cathode. This potentiogram is similar to the one for pyrrole polymerization without Aqd except for the potential drop to zero, i.e. the first contact with the cathode, occurred after ~2.5 sec. All supporting information is incorporated herein in its entirety.

Scanning electron micrograph images of the protein-functionalized Ppy nanowire demonstrated that the nanowire was continuous, well defined, dendrite free, spanning the entire length of the channel, and making a good contact with both electrodes. Energy-dispersive X-ray (EDX) analysis of the nanowires confirmed the presence of Cd within the nanowire, an indication of the presence of quantum dot and thereby streptavidin within the Ppy nanowire The integrity and good ohmic contact with the two electrodes of the biomolecule-modified Ppy nanowire was further confirmed by the linear dependence of current as a function of the applied potential.

To demonstrate the utility of functionalized nanowires as sensors, biotin conjugated to a 20-mer DNA oligo (biotin-DNA) were applied. FIG. 1 shows that the resistance of the 200 nm wide avidin-functionalized nanowires increased rapidly to a constant value upon addition of 1 nM of the biotin-DNA conjugate and the resistance increased with increasing concentrations up to 100 nM. In contrast, addition of buffer and/or DNA oligo without conjugated biotin to the functionalized nanowires did not result in any observable changes in resistance. These observations together with the absence of any response to the addition of biotin-DNA to a unmodified Ppy nanowire confirmed that the changes in resistance was due to the binding of biotin-DNA with avidin in the functionalized nanowires. A similar response of a 100 nm Ppy-Aqd nanowire upon exposure to similar concentrations of biotin-DNA further validated the sensing strategy. While the % changes were very similar to the 100 nm Ppy-Aqd nanowire, as expected the absolute resistance values in 200 nm nanowires was lower due to higher cross sectional area of such nanowires.

FIG. 1 shows the electrical responses of Avidin embedded polypyrrole (200 nm) to additions of 1 μL of A) 1 nM biotin-DNA (single stranded) and B) 100 nM biotin-DNA. The responses were recorded on two separate polypyrrole-Avidin nanowires. Polypyrrole nanowire containing entrapped Avidin were grown using 25 nM pyrrole in 10 mM NaCl and 2 nM of Avidin.

For the detection of larger target analytes that cannot diffuse into the Ppy pores and fast response of small molecules, the entrapped biomolecule should be on the surface of the nanowire. To determine the location of the Aqd in the Ppy, AFM Phaselmaging™ was performed on a 50 nm thick (the depth of the channel used for nanowire formation) Aqd-Ppy film electrochemically deposited on a gold electrode. AFM Phaselmaging™ is an extension of tapping mode which allows detecting variation in composition and hardness. Aqd-Ppy film showed much highly contrast compareed to Ppy film, demonstrating the composite nature of Aqd-Ppy film and presence of Aqd on the film surface.

In conclusion, a facile yet powerful method for fabrication of biologically-functionalized nanowires of controlled dimension and high aspect ratio in confined channels, and its application to bioaffinity sensing was demonstrated. The one-step incorporation of functional biological molecules into the conducting-polymer nanowire during its synthesis and built-in electrical contacts is the major advantage of the new fabrication method over the reported silicon nanowires and carbon nanotubes biosensors that require post-synthesis modification and positioning. Combined with the already demonstrated ability to make individually addressable nanowires that are a few micron apart sequentially, one at a time, will enable fabrication of high-density biosensor nanoarrays. While the concept has been demonstrated for biological modification of Ppy nanowires, other monomers such as aniline and thiophene that can be electropolymerized from aqueous environment benign to biomolecules can also be employed. The diversity of monomers, dopants and electropolymerization conditions adds another dimensionality to the reported technique in terms of the ability to design tailored-made nanowire biosensors.

This example is illustrated in Ramanathan K., et al, J. Am. Chem. Soc. 127(2), 2005, pages 496-497; the contents of which is incorporated herein in its entirety.

EXAMPLE 2

Biomolecule Entrapped Conducting Polymer Nanowire as a Biosensor

Described in this example is a single step, label-free method for entrapping a functional biomolecule (streptavidin) within a conducting polymer (polypyrrole) nanowire and its application to biosensing is demonstrated. The electropolymerization of polypyrrole is carried out between gold electrodes within 100 or 200 nm channels etched on prefabricated silicon wafers. A chronopotentiometric method with a 100 nA step provides a functional nanowire in less than 5 sec. The stable polypyrrole with entrapped streptavidin-quantum dot conjugates is challenged with a biotin-DNA conjugate to generate the sensor response. A proof of concept with two different concentration of b-DNA (0.5 and 100 μM) is demonstrated. Additional evidence using current-voltage and microscopic characterization is also provided.

Experimental—Materials: Pyrrole 98% purity from Aldrich Chemical Company. Multichannel Potentiostat model VMP2 (Princeton applied research) interfaced with EC-lab software. Streptavidin-CdSe (quantum dot) conjugate, from quantum dot Corporation. Biotin-DNA conjugate (Integrated DNA technologies). Microfabricated gold electrodes on silicon wafers (local source). Nitrogen gas 99% purity (Puritan Medical Products). Microcon filter unit 30 kD cut-of (Millipore Corporation). Scanning Electron Microscope (SEM) with Energy Dispersive and X-ray fluorescence (EDAX) capability (Philips, model XL30-FEG). and Atomic force microscope (AFM—Digital Instruments).

Experimental—Methods. Preparation of pyrrole monomer solution: Pyrrole (Py) was distilled prior to use. The pure solution was stored in the dark between 4 and 10° C. to prevent thermal degradation. A nitrogen blanket was maintained in the head space to prevent oxidation of Py by ambient air. A solution of 0.01 M NaCl was prepared in nanopure water (18MΩ resistance), and purged with $N_2$ gas continuously for 2 min followed by addition of Py to yield a final concentration of 25 mM. The solution was mixes thoroughly for uniform mixing and stored in the dark prior to use.

Experimental—Methods. Electropolymerization of polypyrrole (Ppy) between microfabricated gold electrodes: The silicon chip with 100 or 200 nm wide and 3 μm long channels between gold electrodes with $100 \times 100$ $nm^2$ or $200 \times 100$ $m^2$ surface area was used for the galvanostatic deposition of Ppy. The chip was mounted on a probe station and contacted to the gold pads on the chip, with micromanipulator pins. A pseudo-reference electrode was placed about 2 mm from the center of the channel between the gold electrodes. Connecting the electrical leads to the potentiostat completed the circuit. A 2 μl drop of freshly prepared Py solution was placed on the channel and the contact of the reference electrode with the liquid drop was ensured. The oxidative electro-polymerization of Py to Ppy was initiated by applying a 100 nA current step for 10 min through the 2 μl solution. The potential changes on the working electrode were continuously recorded in the chronopotentiometric mode. The electropolymerization process was stopped at a point when the potential showed a sharp drop towards 0.0 V. The leftover monomer solution was siphoned of the electrode surface. The electropolymerization was carried out in the absence of any mechanical, electrical or electrostatic interference. The presence of the nanowire was verified by performing the current voltage (IV) measurement between –0.05 and 0.05V at 10 mV/s scan speed. The slope of the IV was used for evaluating the conductivity of the Ppy nanowire. The thickness of electrochemically grown Ppy film was measured using Dek-tak instrument.

Experimental—Methods. Purification of the streptavidin-quantum dot (Aqd) solution: The Aqd solution consisting of avidin conjugated to Cadmium selenide quantum dots in 2 μM borate buffer pH 8.3, was purified by micro-filtration prior to use. A 10 μl aliquot of the stock Aqd solution was purified using 100 μl washing with nanopure water at least 3 times. The washings through the filters were performed by centrifugation at 12000 rpm for 20 min. The washed Aqd from the filter paper was re-suspended in 100 μl nanopure water and stored at 8-10° C. prior to use.

Experimental—Methods. Electropolymerization of Ppy Aqd nanowire: A 100 μl aliquot of freshly prepared Py monomer solution in 0.01M NaCl was mixed with 1 μl purified Aqd solution. The contents were stirred for uniform mixing. A 2 μl drop of this solution was placed on the electrode surface and the electro-polymerization initiated as described above.

Experimental—Methods. Response measurement of Ppy-Aqd nanowire to biotin-DNA (b-DNA) conjugates: To the surface of a freshly grown Ppy-Aqd nanowire a freshly diluted solution of b-DNA conjugate was added. A 0.5 μM and 100 μM concentration of b-DNA was used for these studies. The resistance changes of the Ppy-Aqd nanowire to sequential additions of nanopure water, 0.5 uM and 100 uM b-DNA were monitored online. The results were re-plotted in Origin (version 7.2) for data analysis. A Ppy nanowire without Aqd was used as a control for the response measurements.

Experimental—Methods. SEM, EDAX and AFM measurements: All these measurements were performed directly on the Ppy and Ppy-Aqd nanowires. Both SEM and EDAX were performed simultaneously using a 10 kV beam and a spot size of 3. The fluorescence from the Cd contained in the Ppy-Aqd nanowire was compared with the control. The AFM was recorded on a galvanostatically grown film of Ppy and Ppy-Aqd on gold electrodes using a $100 \times 100$ μm scan area at 10 μm/s scan speed. The images were generated on a n-Surf software capable of providing 3-dimensional phase and height images.

Results and Discussion:

Single step growth and functionalization of Ppy nanowires with an entrapped biomolecule is achieved in the present studies. The biomolecule (Aqd) is captured from the solution phase into the Ppy chains while maintaining its functionality. The Cl⁻ doped Ppy resulting in a p-type doping of the Ppy forms the nanowire within the pre-defined 100 or 200 nm dimension channel between prefabricated gold nanoelectrodes. The exposed gold electrodes (3 μm×$10^4$ $nm^2$) at the ends of the channel along with the reference electrode complete the electrical circuit, after addition of the 2 μl drop on the electrode surface. The electrolytic process is initiated using a 100 nA current step resulting in nucleation and growth of Ppy from the anode to the cathode. The confinement of the nanowire within the channel is dependent on diffusion of the monomer solution within the channel and absence of any air bubbles in the path of the current during the oxidative electropolymerization. The hydrophobicity of the photoresist in addition to the ability of the solution to wet the channel surface, controls the diffusion of the monomer solution into the channel.

The positioning of the reference electrode may be important to the monitoring of the potential changes on the working electrode. The loss of contact of the reference electrode with the 2 μl solution drop results in an open circuit condition and lead to a rapid increase in voltage to about 12-14V. The evaporation of the drop may also be important as it leads to concentration changes of the monomer on the electrode surface. However, within the experimental conditions up to 10 min these changes are found to be insignificant for the nanowire formation. It is observed the edges of the drop start receding after about 15 min after placing the drop. In addition, as the Py monomers already diffuse within the channel contribute to the nanowire formation and surface evaporation from the drop, plays an insignificant role in this regard.

Figure 2:
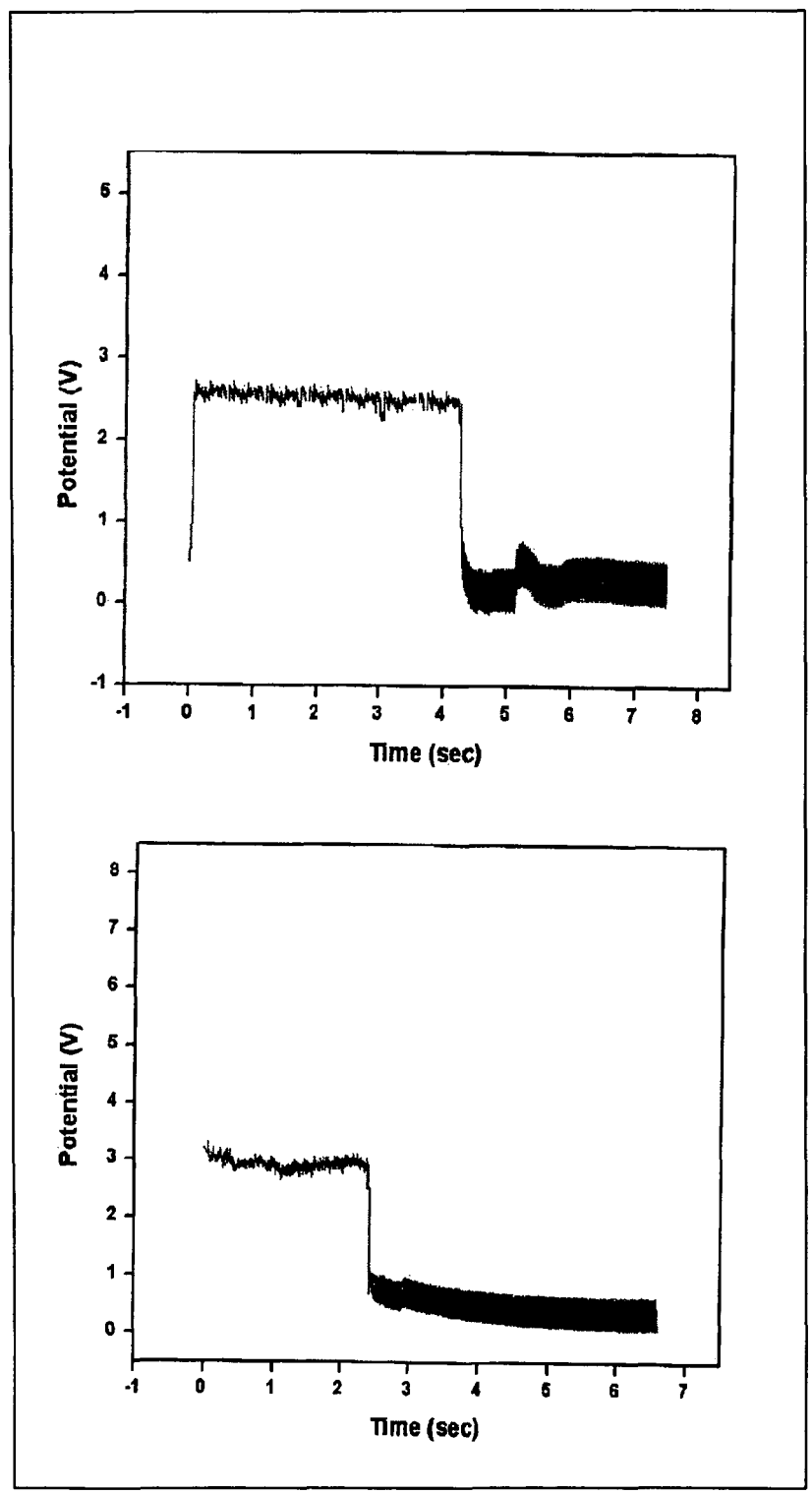
FIG. 2 shows that upon impressing a 100 nA current to the quiescent solution drop on the electrode surface, the potential of the working electrode rapidly increases from the open circuit voltage to a value between 2.8 and 2.9V.

As shown in FIG. 2A upon impressing a 100 nA current to the quiescent solution drop on the electrode surface, the potential of the working electrode rapidly increases from the open circuit voltage to a value between 2.8 and 2.9V. This may be attributed to the rapid nucleation and initiation of Ppy growth on the gold surface, with additional contributions due to the equilibrium between the $Py_{(ox)}$ and $Py_{(red)}$ forms of the Py monomer. The polymerization proceeds via a radical cation formation of the Py monomer that reacts with the next radical cation to give a dimer with elimination of two protons. The Ppy is formed by α-α' bonding between consecutive Py radicals. During the continued electrolysis there is downward slope (2-3 sec) of the chronopotentiogram that may be attributed to the shift in the equilibrium concentrations of the Py(red) and the Py radical cations. It is unclear at this stage if this could be correlated to the elongation of the Ppy chain towards the opposite electrode. The Ppy chain growth may be terminated by unreactive Py radical or steric hindrance. However, due to the 3 μm spacing between the electrodes and 300 pL channel volume, the polymerization proceeds fast and fills the channel in less than 5 sec.

The formation of the Ppy nanowire and contact with the opposite gold electrode results in a sharp dip in the chronopotentiogram towards 0.0 V. A similar dip was observed for Ppy-Aqd nanowire FIG. 2B. However, the tip of contact in this case was about 4.3 sec as compared to 2.5 sec in case of Ppy. The nanowire formation is terminated within 5 sec after the dip is observed. Attempts to stop the electropolymerization exactly at the dipping point may result in an unstable contact of the Ppy nanowire with the gold electrode. However, continued electrolysis for more than 5 sec beyond the dip results in overgrowth and an ill-defined nanowire. After the nanowire formation the 100 nA current preferentially flows through the nanowire (the shorter path) compared to the solution phase.

Figure 3:
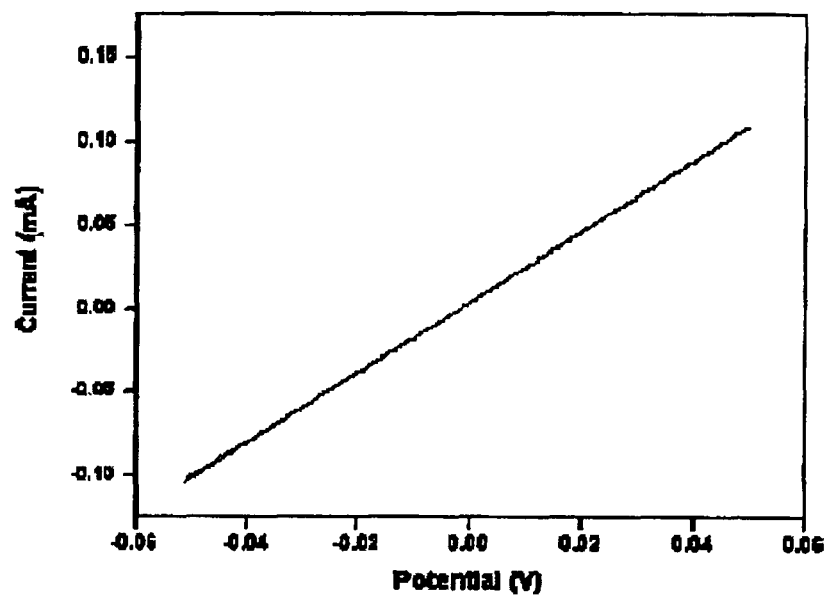
FIG. 3(A-B) shows IV measurements on Ppy-Aqd and Ppy nanowires.
Figure 3:
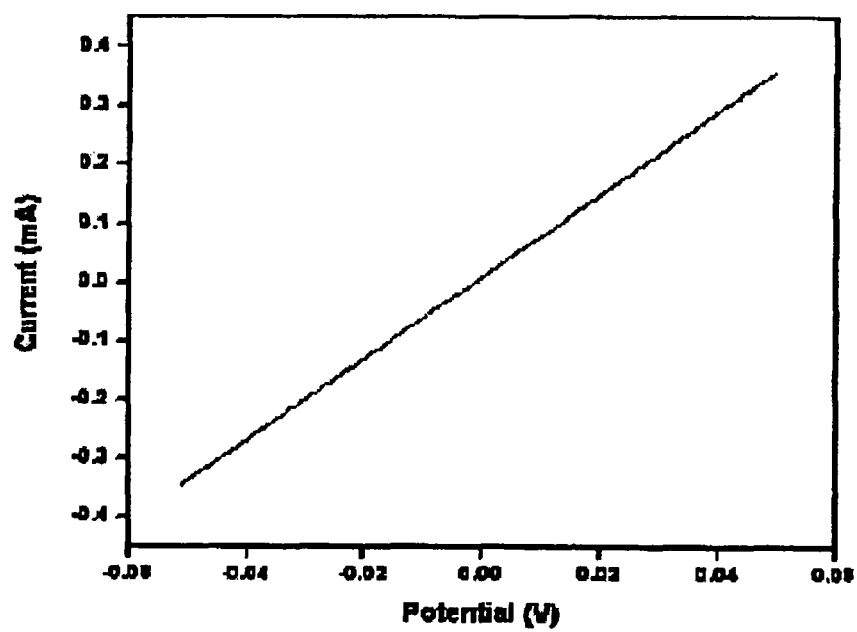

The integrity and stability of the Ppy-Aqd and Ppy nanowires are confirmed by performing the IV measurements (FIGS. 3A and B). The slope of the IV provides the conductance of the nanowire and considering identical cross sectional area ($10^4$ nm$^2$) and length (3 µm) of the nanowires, the conductivities are comparable. The conductance of the Ppy-Aqd (1.875 mS-FIG. 3a) is found to be higher than Ppy (0.75 mS-FIG. 3b). This is consistent with the incorporation of a negatively charged species into the p-type Ppy chains and the fact that Aqd is negatively charged at the pH of our measurements. Similar to Cl$^-$ the negatively charged Aqd molecule participates in causing depopulation of the bonding p-orbital with the injection of holes in Ppy. This increases the number of charge carriers and thereby leading to an increase in conductivity of Ppy-Aqd. In addition the linear nature of the IV points out to an ohmic contact between the gold electrode and Ppy nanowire.

In addition to the IV characterization of the Ppy nanowires in the presence and absence of entrapped Aqd, microscopic investigations were carried out to confirm the presence of Aqd within the nanowires. SEM images of the nanowires show the well-confined nature of the nanowire in the presence and absence of Aqd. In addition the EDAX performed on such nanowires confirmed the presence of a Cd peak in the Ppy-Aqd nanowire. The presence of Cd is indicative of the presence of the quantum dot (CdSe) within the Ppy nanowire and provides an indirect evidence of Avidin entrapment as it is conjugated to the Aqd. Detailed investigations suggest the bonding between Aqd and the CdSe quantum dot is covalent in nature and is not denatured under the conditions of the experiment. The presence of C, O, Na, Si, Au and Cl peaks also indicate the presence of Cl$^-$ doped Ppy nanowire. As a further confirmation the AFM images recorded on Ppy films in the presence and absence of Aqd clearly demonstrated the presence of spherical beaded topology of Aqd containing films versus the smooth films of Ppy. The corresponding phase images also confirm this finding. These results ascertain the ability of electropolymerized Ppy films to entrap Aqd within their structure during the electropoymerization process.

Figure 4:
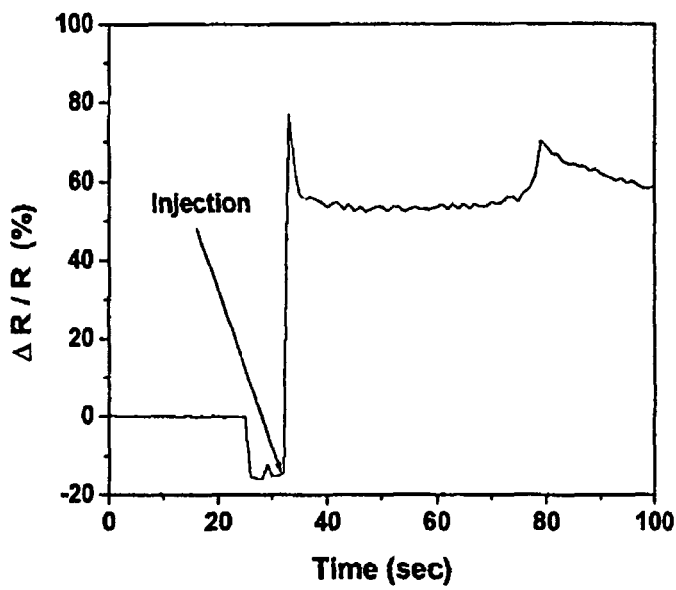
FIGS. 4(A, B, and C) and 5(A, B, and C) show nanowire responses to additions of b-DNA.
Figure 4:
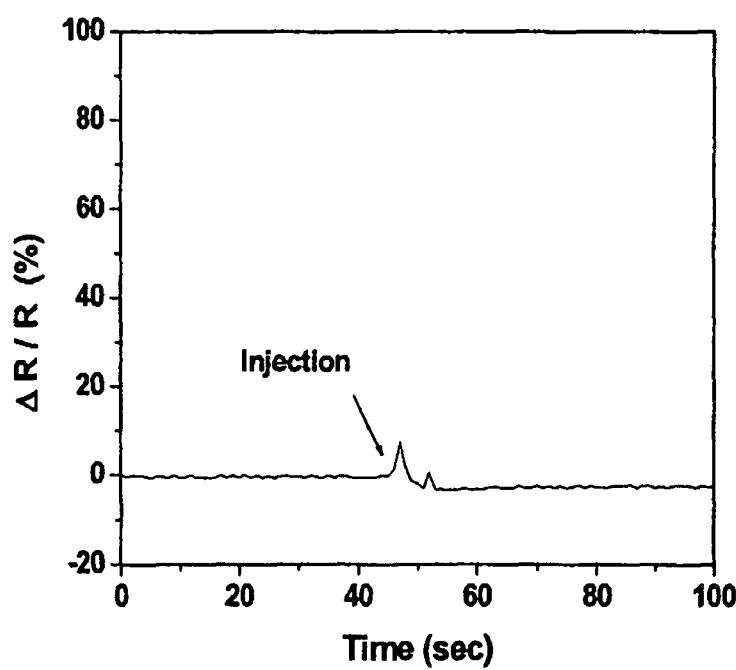
Figure 4:
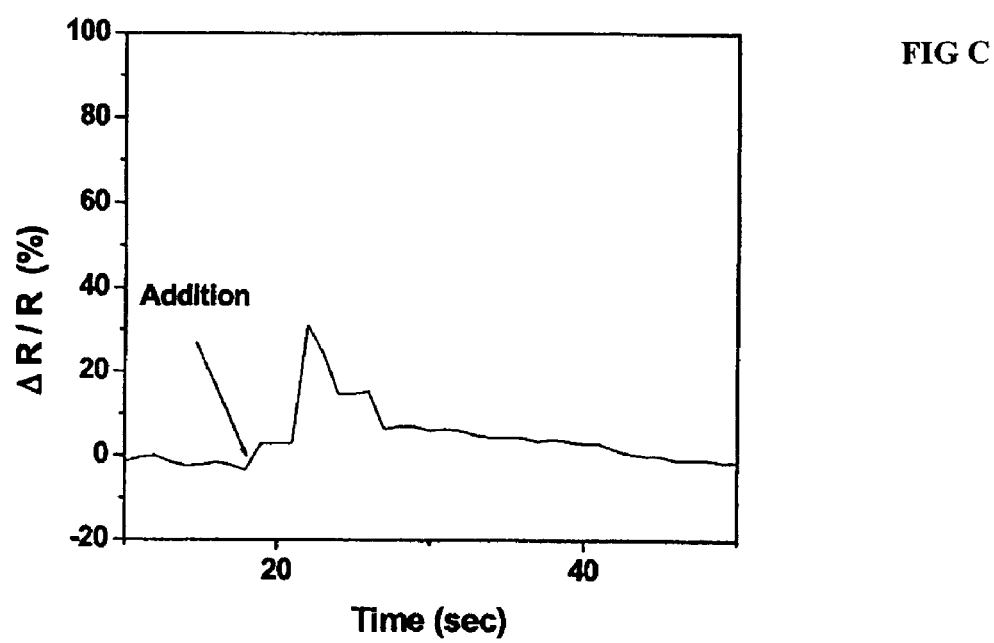
Figure 5:
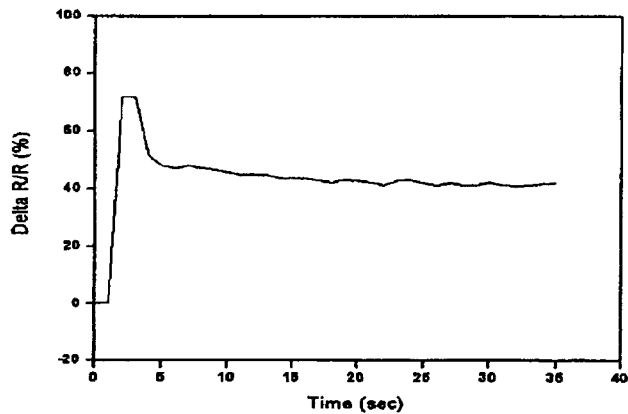
Figure 5:
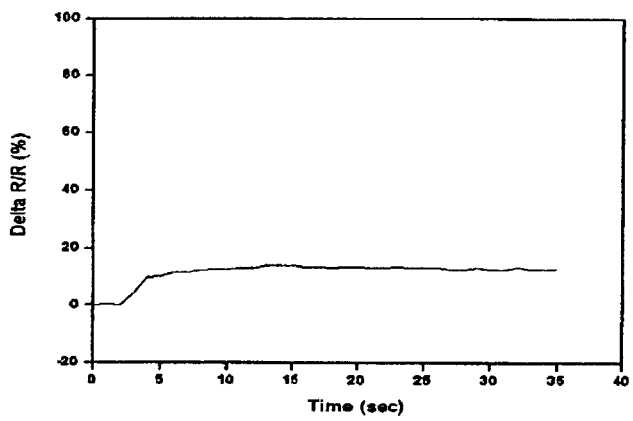
Figure 5:
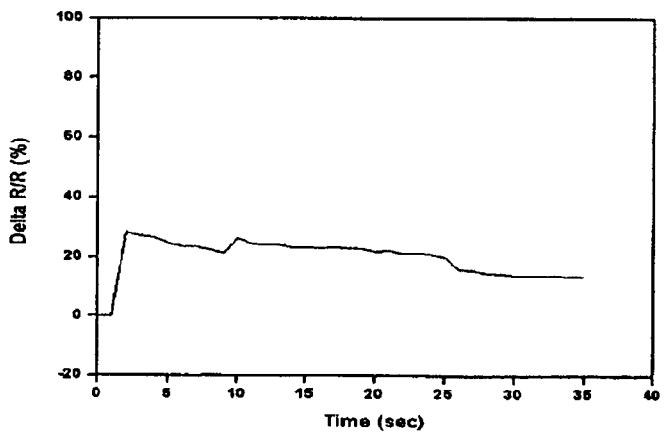

The confined nanowire obtained both in the presence (FIG. 4A-C) and absence (FIG. 5A-C) of Aqd was employed for studying its response to additions of b-DNA. The well-characterized ligand-receptor binding of biotin-streptavidin was exploited for the detection of the b-DNA conjugate. The binding event results in either accumulation or depletion of charges within the Ppy structure that could be employed for biosensing purposes. As shown in FIG. 4A, the addition of 100 µM b-DNA to a 100 nm Ppy-Aqd nanowire resulted in a rapid increase of resistance with a 50% change as compared to the control (FIG. 4B). The decrease in conductance or increase in resistance of the Ppy-Aqd nanowire could be attributed to the rearrangement of the negative charges between the Ppy-Aqd and b-DNA structures. The binding results in repletion of holes in the Ppy structure with electrons that were abstracted earlier by the Aqd molecule. However this effect is only about 10% in the absence of Aqd. This clearly suggests that the binding of b-DNA to Aqd causes a substantial structural change of the streptavidin molecule resulting in reallocation of the charges within the Ppy-Aqd nanowire. This effect (30% change) was also observed for lower concentration of b-DNA (0.5 um) as shown in FIG. 4C. To further validate this sensing strategy, a 200 nm Ppy-Aqd nanowire was exposed to similar concentrations of b-DNA. As shown in FIG. 5 A-C, the % changes were very similar to the 100 nm Ppy-Aqd nanowire. The absolute resistance values in both the 100 nm and 200 nm nanowires suggests the lower resistance of the 200 nm nanowires due to higher cross sectional area of such nanowires. This response of the Ppy-Aqd nanowire to b-DNA demonstrates the ability of obtaining a single step incorporation of a sensing biomolecule within a conducting polymer structure and employing the same for fabrication of a label-free nano-biosensor.

EXAMPLE 3

Individually Addressable Conducting Polymer Nanowires Array

The following is an example that has been carried out of the sysnthesis and use of one conducting polymer nanowire as described in this patent. This examples has been described in Ramanathan, K.; Bangar, M.; Yuri, M.; Chen, W.; Mulchandani, A.; Myung, N. V., Nano Lett., 2004, 4, 1237-1239, the contents of which is incorporated herein by reference in its entirety.

Described is a facile technique for fabrication of individually addressable conducting polymer nanowires array of controlled dimension, high aspect ratio, and site-specific positioning using electrodeposition between electrodes in channels created on semiconducting and insulating surfaces that can be easily scaled-up is reported. In addition, the ability to create "arrays" of conducting polymer nanowires of same or different materials on the same chip has been demonstrated. The fidelity, quality, and electrical properties of single polypyrrole and polyaniline nanowire have been examined by SEM and I-V characteristics. The dendrite free conducting polymer nanowires completely confined within the channels with full dimension control were observed. I-V characteristic of such nanowires show the ohmic nature of the contact with Au electrode.

Nanowires and nanotubes are promising materials for a variety of applications including optical and electronic nanodevices, and chemical and biological sensors. (He, H. et al., *Encyclopedia of Nanoscience and Nanotechnology*, Nalwa, H. S., Ed. American Scientific Publishers: New York, Vol. X, pp. 1-18 (2003)) Successful application of these nanostructured materials into functional nanodevices requires controlled patterning at micro- and nano-meter scale. Semiconductor and metal nanowires (NWs) and carbon nanotubes (CNTs) have been the materials of choice for fabricating sensor devices. Although several examples of uses of these material: as nanosensors have been reported, many properties of these materials and fabrication methods have significantly limited their full-scale development, particularly for high density arrays. (Cui, Y. et al., *Science* 293:1289-1292 (2001); Kong, J. et al., *Science* 287:622-625 (2000); Li, C. Z. et al., *Appl. Phys. Lett.* 76:1333-1335 (2000); Favier, F. et al., *Science* 293:2227-2231 (2001)) For example, 1) current synthetic methods are unable to selectively grow sensor-suitable semiconducting CNTs, 2) limitation of dopants and inability to functionalize materials other than silicon limits the diversity of semiconductor NWs, 3) nanodevices fabrication requires complex post-synthesis assembly using sophisticated manipulating tools and 4) functionalization/modification for incorporation of specific sensing capabilities can only be performed post-assembly.

Conducting polymers are emerging as a promising material for synthesis of nanostructured materials and devices. They are particularly appealing because they exhibit electrical, electronic, magnetic and optical properties similar to metals or semiconductors, while retaining their flexibility, ease of processing and modifiable electrical conductivity. The electrical conductivity of these polymers can vary from an insulator to almost the metallic state and be reversibly modulated over 15 orders of magnitude by controlling the dopant type and level (MacDiarmid, A. G. *Synth. Met* 125:11-22 (2002); Heeger, A. J. *Synth. Met.* 125:23-42 (2002); Shirakawa, H. *Synth. Met.*, 125:3-10 (2002)). Their porous structures are very amenable to entrapping biomolecules. (Ramanathan, K. et al., *Sens. & Act.* B 21:165-169 (1994)) A variety of conducting polymers have shown promise as sensor materials, including biosensors, because their properties can be tailored to detect wide range of chemical compounds. (Dai, L. et al., *Pur. Appl. Chem.* 74:1753-1772 (2002); Bidan, G. *Sens. & Act.* B 6:45-56 (1992); Schuhmann, W. *Enzyme and Microbial Biosensors: Techniques and Protocols, Mulchandani*, A. & Rogers, K. R., Eds. Humana Press: Totowa, N.J., pp. 143-156 (1998)) While the properties of conducting polymers offer many advantages over semiconductor and metallic NWs and CNTs, application of these materials for high density nanosensors array is limited by some of the similar problems. Although successful in satisfying some criteria, photolithography, (Jager, E. W. H. et al., *Science* 290:1540-1545 (2000)) microcontact printing, (Yu, J. F. et al., *Chem. Commun.* 1274-1275 (2001)) template assisted synthesis, (Marck, C. et al., *J. Chem. Mater.* 13:747-752 (2001)) scanning electrochemical microlithography, (Martin, C. R. *Chem. Mater.* 8:1739-1746 (1996)) mechanical stretching (He, H. X. et al., *J. Appl. Phys. Lett.* 84:828-830 (2004)) and electrochemical dip-pen lithography (Maynor, B. W. et al., *J. Am. Chem. Soc.* 124:522-523; (2002)) techniques for fabricating micro- and nano-scale structures from conducting polymers still have limitations in terms of yield, resolution, material multiplicity, positioning, production of high density array and most of all cost.

As discussed above, we have invented a facile technique for synthesis of micron/sub-micron width metallic and conducting polymer wires by electrodeposition within channels between two electrodes on the surface of silicon wafers. (Yun, M. et al., *Nano Lett.* 4:419-422 (2004)) In this example, we extend this method to synthesize single and multiple individually addressable controlled dimension, high aspect ratio (100 nm wide by up to 13 μm long) and dendrite-free nanowires of conducting polymers polyaniline and polypyrrole. In addition, we demonstrate the ability to create scalable high density "arrays" by site-specific positioning of conducting polymer nanowires of same and different composition on the same chip.

The deposition and growth of the nanowire chains are based on well known electrochemical oxidative polymerization starting with monomers and dopants. Multiple channels can be etched between gold electrode pairs in the form of arrays, to provide formation of any number of individual nanowires. The procedure is a single step deposition process for each nanowire and multiple nanowires array, of different materials can be deposited on the same wafer sequentially. Polypyrrole (PPY) and polyaniline (PANI) are used as models for demonstration.

The fabrication of the electrode structure used for the growth of the conducting polymer wire was described elsewhere. (Yun, M. et al., *Nano Lett.* 4:419-422 (2004)) In a typical experiment, the electrode chip/wafer is mounted on a probe station and the contact is established using metallic pins. The contact pins are precleaned with isopropanol. A three electrode set-up is used for the deposition. Two microliters of deoxygenated pyrrole (0.06 M in 0.01 M KCl) or aniline (0.1 M in 0.1 MCl), was placed in the electrolyte channel between the two electrodes and the electropolymerization was performed under galvanostatic mode by applying a desired current while the potential of the working electrode was monitored continuously with respect to a pseudo reference electrode. Simultaneously a multimeter (connected in the circuit) was programmed to record the resistance values every 1 s and continuously transfer data to a computer file. The electropolymerization was initiated by impressing a 100 nA current between the two gold electrodes. Typically, the potential rises from the open circuit potential to a value of 2 V followed by a gradual decrease as the wire grew. When the wire was fully grown and made a contact with the cathode, the potential dropped to 0.6 V for PANI and 0 V for PPY. At this time, the process was terminated, the electrolyte solution siphoned out, the wafer rinsed three times with deionized distilled water and dried. The resistance, on the other hand, started from a value of 20 MΩ and decreased to a few KΩ. The evaporation of water from the 2 μl drop was minimal and did not affect the process at least up to 4 min.

After formation, resistance of the nanowire was 0.2-0.8 kΩ (wet) and 6-7 MΩ (dry) for a 500 nm wide nanowire, while it was about 1 MΩ for a 100 nm wide dry nanowire. The resistance of the nanowire in the dry state was dependent on the thickness and uniformity of the nanowire, humidity levels and the deposition conditions. The nanowire resistance was stable at least for 9 hr after formation. In the absence of the monomer, nanowire formation was not observed.

We performed SEM on an exemplary nanowire. The SEM displayed a 100 nm wide and 4 μm long electrochemically grown PANI nanowire. As observed, the nanowire is continuous, well-confined, non-dendrite, spanning the entire length and making contact between the two electrodes. The quality and fidelity of the nanowire obtained in this study is far superior compared to the earlier work where the overgrowth is clearly observed even in the optical images at the ends of wires that are 5 to 10-fold thicker. (Yun, M. et al., *Nano Lett.* 4:419-422 (2004))

Figure 6:
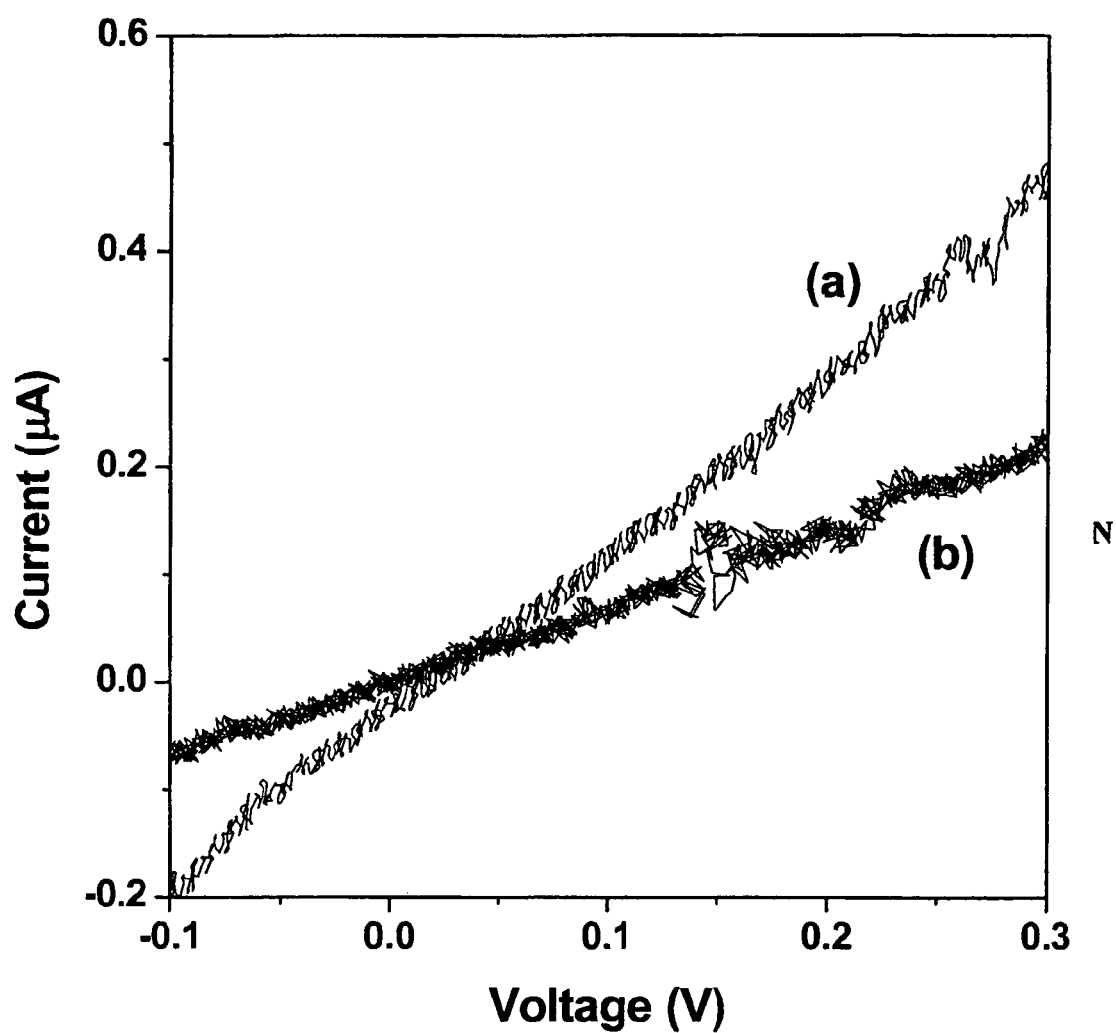
FIG. 6 shows the current vs. potential for a PANI (a) and PPY (b) at 50 mV/s scan rate.

To confirm the wire integrity and contact with the gold electrodes, current vs. voltage studies were performed for dry PANI and PPY nanowires (FIG. 6). A linear dependence of the current on the applied potential confirmed ohmic contact at both electrodes necessary for the passage of current through the nanowire in dry state.

The ability to make individually addressable nanowire in high density was evaluated by making two 200 nm wide by 2.5 pm long PPY nanowires separated by 6 μm sequentially. An SEM image demonstrateed that fabrication of arrays of, electrodeposited wires of same or different material at precise location was feasible.

In multiple deposition studies uniform nanowires between 0.5 and 13 μm in length within 1 μm, 500 nm, 200 nm and 100 nm wide channels were formed from both PANI and PPY. While the electropolymerization in this work was performed using aniline and pyrrole in aqueous medium, the methodology can be extended to electropolymerization of other conducting polymer monomers and also non-aqueous medium.

For demonstration of the conducting polymer nanowire as sensor, the change in resistance of PANI as a function of environment pH was evaluated. Addition of 0.1 M HCl decreased the resistance by 4 orders. The resistance could be switched by 2-3 orders of magnitude by repeatedly cycling with water and 0.1 M HCl. A similar but lower resistance change was observed for PPY. The 4-order of magnitude resistance change observed with the nanowire illustrates the superiority of nanowires over micron or sub-micron wires. (Yun, M. et al., *Nano Lett.* 4:419-422 (2004))

In summary, we report a facile technique for fabrication of conducting polymer nanowires of controlled dimension and high aspect ratio using single step electrodeposition between electrodes in channels created on insulating surfaces. The technique is capable of producing arrays of individually addressable nanowire sensors, with site-specific positioning, alignment and chemical compositions. The diversity of monomers, dopants and electropolymerization conditions, for e.g. monomer and dopant concentration, solvent and deposition mode, can provide "tailored" materials for specific applications. Additionally, the benign operating conditions for electropolymerization make this process ideal for fabrication of nanobiosensors by the direct deposition of conducting polymer nanowires with embedded bioreceptors in one step rather than multiple steps needed in surface-modified nanowires and CNTs.

EXAMPLE 4

*Electrochemically grown wires for individually addressable sensor arrays,* Minhee Yun et al, Nanoletters 4(3), 2004, pages 419-422; the contents of which is incorporated herein in its entirety.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A device for detecting an analyte, the device comprising:
   a first and a second electrode;
   a single, continuous doped conducting polymer nanowire connecting the first electrode to the second electrode; and
   a circuit connected to the first and the second electrode for monitoring an electrical characteristic of the nanowire between the first and the second electrode;
   wherein the doped conducting polymer nanowire is made of a doped conducting polymer material comprising an analyte-binding species incorporated into a conducting polymer material;
   wherein the analyte-binding species is capable of binding to an analyte; and
   wherein the electrical characteristic of the doped conducting polymer material in contact with a composition comprising the analyte is different from the electrical characteristic of the doped conducting polymer material not in contact with a composition substantially free of the analyte.

2. The device of claim 1, wherein
   the analyte-binding species and analyte are selected from the group consisting of natural and synthetic antibodies and antibody fragments and their corresponding antigens;
   natural and synthetic proteins and protein fragments and their corresponding ligands;
   receptors and their ligands;
   natural and synthetic polynucleotide and oligonucleotide sequences and their complementary sequences;
   single and multiple strand, natural and synthetic nucleic acids and species binding to such single and multiple strand nucleic acids; and
   DNA aptamers and their ligands.

3. The device of claim 1, wherein the conducting polymer material is selected from a polyacetylene, polyaniline, polythiophene, polypyrrole, polyarylene, polyphenylene, poly (bisthiophenephenylene), poly-methylpyrrole, conjugated ladder polymer, poly(arylene vinylene), poly(arylene ethynylene), an organic derivative thereof, or an organometallic derivative thereof.

4. The device of claim 1, wherein the polymer material is polypyrrole.

5. The device of claim 4, wherein the analyte-binding species is avidin or a derivative of avidin.

6. The device of claim 5, wherein the analyte is biotin or a derivative of biotin.

7. The device of claim 1, wherein
   the composition to be contacted with the doped conducting polymer material is a solid composition,
   a gaseous composition,
   a powdered solid composition, or
   an aerosolized composition.

8. The device of claim 1, wherein the electrical characteristic is resistance.

* * * * *